US009186523B1

(12) United States Patent
Zolli

(10) Patent No.: US 9,186,523 B1
(45) Date of Patent: Nov. 17, 2015

(54) GLAUCOMA VISION IMPLANT—AN ARTIFICIAL VISION PROSTHESIS AND MONOCONAL (VERTICAL) THEORY OF COLOR VISION—EMPHASIZING PHYSICS

(71) Applicant: Christine Lydie Zolli, Oldwick, NJ (US)

(72) Inventor: Christine Lydie Zolli, Oldwick, NJ (US)

( * ) Notice: Subject to any disclaimer, the term of this patent is extended or adjusted under 35 U.S.C. 154(b) by 0 days.

(21) Appl. No.: 14/305,768

(22) Filed: Jun. 16, 2014

(51) Int. Cl.
*A61N 5/06* (2006.01)
*A61N 1/36* (2006.01)

(52) U.S. Cl.
CPC .......... *A61N 5/0622* (2013.01); *A61N 1/36046* (2013.01); *A61N 2005/0643* (2013.01); *A61N 2005/0652* (2013.01)

(58) Field of Classification Search
CPC ...... A61K 9/0051; A61F 9/08; A61N 1/0543; A61N 1/36046
USPC ...................... 607/54, 60; 604/294; 623/11.11
See application file for complete search history.

(56) References Cited

U.S. PATENT DOCUMENTS 5,627,921 A * 5/1997 Lidgard et al. .................. 385/12
5,800,530 A * 9/1998 Rizzo, III ...................... 623/6.22
2006/0173397 A1* 8/2006 Tu et al. ............................ 604/8
2007/0005116 A1* 1/2007 Lo ................................... 607/54
2008/0086206 A1* 4/2008 Nasiatka et al. ............. 623/6.14
2009/0105817 A1* 4/2009 Bretthauer et al. ............ 623/4.1
2010/0094382 A1* 4/2010 Pezaris et al. .................. 607/54
2010/0249877 A1* 9/2010 Naughton ....................... 607/54

* cited by examiner

*Primary Examiner* — Carl H Layno
*Assistant Examiner* — Erin Piateski
(74) *Attorney, Agent, or Firm* — Hess Patent Law Firm LLC; Robert J. Hess

(57) ABSTRACT

An apparatus and method of placing a glaucoma vision implant, including a vision restoring prosthesis; enclosing the vision restoring prosthesis with, a transparent casing, the vision restoring prosthesis including a photoreceptor component and a nano-fiber optic bundle component. The photoreceptor component is wirelessly powered and includes a microelectronic artificial vision array that carries micro photodiodes and has a shape of an intraocular cataract lens. The microelectronic artificial vision array is implanted behind a pupil of an eye. The nano-fiber optic bundle component abuts a lateral geniculate nucleus and may include the micro photodiodes and/or electrodes that abut by negotiating insertion of the nano-fiber optic bundle component into an optic nerve and an optic tract to reach the lateral geniculate nucleus. The lateral geniculate nucleus is stimulated to process vision by the nano-fiber optic bundle component.

16 Claims, 8 Drawing Sheets

GLAUCOMA VISION IMPLANT—AN ARTIFICIAL VISION PROSTHESIS AND MONOCONAL (VERTICAL) THEORY OF COLOR VISION—EMPHASIZING PHYSICS

BACKGROUND OF THE INVENTION

I am a licensed, board certified opthalmolgist holding academic appointments as an associate surgeon at Wills Eye Hospital (Philadelphia, Pa.) and associate clinical professor at University of Medicine and Dentistry of New Jersey (Newark, N.J.).

I am here-to-forth proposing a new theory of color vision: a monoclonal (vertical), i.e., "single-conal" theory of color vision. It is based upon postulating that all cones in the retina are anatomically and functionally the same as receptors of light. Some cones may look more svelte as they are packed closer together and thinner looking because they are more numerous and compacted in the fovea. However, anatomically and functionally they are all the same.

My "single-conal" or "monoconal (vertical)" theory of color vision is therefore contrary to what is currently the standard theory of color vision, namely, the Young-Helmholtz theory that postulates that in the retina there are three discrete types of cones, which are the receptors of light and are spatially apart. That theory is name for researchers Thomas Young (1802) and Herman von Helmholtz (1850).

The reason why the cones are all the same in my view is because:

1) They look anatomically the same (i.e., their outer segments) by light and electron microscopy.

2) On light microscopy slides, transverse sections of cones stain all the same (red) as compared to blue-staining rods when seen with Mallory's Triple Stain per FIG. 107 in Eugene Wolf's "Anatomy of the Eye and Orbit", revised by Roger Warwick, W. Saunders, Co. 1976. Library or Congress Catalogue #76-17429, ISBN: 0721691242, page 107.

3) Blending of ions and chemical reactions is needed to establish the hues we see. To achieve this vertically in outer-cone segments is more plausible then in spatially separated three cones—unlikely the chemical s would diffuse across physical space between the cones without there being debris in the space or without there being dendrites to connect the outer-cone segments for the complex reactions needed to give us sensation of color—for we instantly and continuously perceive things around us in color—and we see 15000+ color hues as catalogues in the registry of colors.

I hold that the cones all function in unison when light enters the retina, but that they are vertically differentiated in their outer-segments as to the depth of reach of light through the stacks of discs. All colors would come about from light penetrating vertically into the depth of cone outer processes. The role of these vertically-differentiated outer-segments would be to break up the visible light into spectrum of wavelengths.

For instance, the red wavelength known to be the longest, slowest, and going-furthest into the depth of the cone outer-segment would be carrying photons of different intensity and would be absorbed at different levels by red sensitized opsins than the shorter blue and green (and in between) wavelengths.

The outer segment discs are termed "refractile" in Fine, Ben S. & Lorenz E. Zimmerman's "Observations on the Rod & Cone Layer of Human Retina.", Investigative Ophthalmology, vol. 2, number 5, p 446-459, October 1963. The outer segment discs might also act as micro-Fresnel prisms further breaking up light into components. Also, chemically different opsins would be positioned at different loci into the stacks.

The light reflected from an image producing object is already differentiated into its special intensity into darker and lighter zones (due to uneven absorption of the reflected light by different colors in the image producing object). Upon entering the retina, the reflected light is captured in different depths of the outer segments by opsins positioned in different levels.

I theorize that as the light is traveling almost instantaneously (traveling at a speed of 186,000 miles per second in vacuum), this photonic latent image, aided by the presence of micro-tubules (thin, biologic nanotube photonics) in axons of cones and rods is beamed up to the lateral geniculate body nuclei in which is then transduced into patterns of images.

The outer segments of cones and rods would, in my view, decompose light into spectral wavelengths and patterns, but then, I would take the color vision factory out of retinal cells and place it in the lateral geniculate body of the thalamus.

Through phylogenic evolution, the retina splits the spectrum of wavelengths of visible light energy and obtains the color image it carries subtractively for the human eyes to see. I propose that the stacks of discs in the outer segments of rods and cones may be vertically differentiated with vertical opsins ("dye couplers") residing at different loci as to the depth so as to dissociate light into wavelengths going vertically into them, thus giving rise to the sensation of color. One might make an analogy of the splitting of the spectrum of wavelengths of visible light energy through phylogenic evolution by the retina with the splitting of the spectrum of wavelengths of light by layers of color film (motion-picture film or Kodakchrome 35 mm).

Just as hydrogen atom is the same on earth as it is on the sun and elsewhere, in light energy and of obtaining the color image it carries subtractively for the human eye to see.

Color film (e.g., Kodak chrome introduced in 1935 and Gaspar color of 1933) for movies and prints is indicative of a process of capturing spectral energy of light to reproduce in color the world around us and was instrumental as the basis for subsequent color capturing devices such as prints, color copiers, television, video cameras, color printers, etc. These all use sophisticated layered chemistry to capture subtractively the light.

Color film is a multi-layered emulsion that uses subtractive primaries, i.e., dyes of yellow, magenta, cyan as couplers arranged vertically in that order embedded in gelatin emulsion to capture blue, green and red wavelengths of light respectively. The layers also include silver halide cloud of micro particles which when exposed to light create black-and-white image as they are converted to metallic silver.

The method of capturing color images of things by selective absorption of wavelengths as light travels perpendicularly down the sandwich of layers is analogous to structures of retinal cone outer segments for color vision processing.

I postulate that the stacks of discs in outer processes of rods and cones of the retina serve similarly as biologic multilayer emulsion structures that very well may be decomposing light into wavelengths.

In this model, any cone outer segments would be able to process blue, green and red wavelengths of light by capturing the different wavelengths at different loci as light progresses down the stacks of discs. If getting color out of electromagnetic energy may be done only in the same way as is done for color film, then such could be similar to what the retina does through the phylogenic evolution.

Cone outer segments are made of stacks and discs one on top of the other with ground substance areas between stacks and continuing with extra cellular ground substance, as described by Fine and Zimmerman in "Observations on the Rod & Cone Layer of Human Retina.", Investigative Ophthalmology Vol. 2, Number 5, pages 446-459, October 1963 (hereinafter referred to as Fine and Zimmerman).

The ground substance mentioned in Fine and Zimmerman is possibly an analogy to the emulsions found in color film. Given that there are several ways emulsions could be used in light of the three cone color theory of Young, a king of "patch work quilt" picture could have arisen for color film if three separate tray pools of different color emulsions were used in a horizontal pattern requiring a large area and mirrors to direct a beam of light to go into each pool. Instead of that approach, the emulsions are stacked vertically one on top of the other to produce viable color images.

Quoting with permission from page 30 of "Exploring the Color Image", publication # H-188, Entertainment Imaging, Eastman Kodak Co., Rochester, N.Y. 14650, Catalogue #8125320—Library of Congress card #9614949 ISBN: 087985-785-4, but may analogy comments are inserted between braces { }:

The three, color records of film are stacked with the fast and show cyan dye forming layers (the read light sensitive record) at the bottom; the magenta layers (the green sensitive record) next up, and the yellow layers (blue sensitive record) on top. The blue record goes on top because all forms of silver halide are sensitive to blue light. The yellow filter beneath the blue sensitive layer keeps blue light from penetrating deeper into the film {retina analog here is lutein-as yellow "filter" which is the yellow color in Macular lutea} and forming unwanted latent images in the magenta and cyan layers. Each color record is separated from its neighbor by a gelatin layer. This prevents silver development in one record from causing unwanted dye formation in another.

Other special purpose layers include a UV-filter layer on top of the pack, {analogy with eye-UV blocked by cornea and lens} because Silver Halide is sensitive to ultraviolet light. {What could substitute for silver micro particles in outer segments of retinal rods and cones? Perhaps CA+2-calcium doubly charged positive ion, which is found in abundance in the outer segment.}

A black antihalation layer prevents reflected light form the film support from scattering back up into the tripack. Such diffuse back scattered light degrades sharpness and is most noticeable as a "halo" around bright objects. In many motion picture films, this antihalation protection is provided by a layer of finely-divided carbon on the back of the film, called "Rem-jet", it is scrubbed off during process. {Analog to the retina is the black retinal pigment epithelium, which is also a light absorbing tissue that may serve to keep the light from scattering back into the stacks of discs of outer segments of cones, thereby preserving sharpness of images we see}.

Proposing that just like in the layers of Kodak color film, the stacks of discs in the outer segments of rods and cones may be vertically differentiated with different opsins (dye couplers) residing from inside-outward at different positions trapping blue light energy nearest, green in the middle and red at the end of the stacks with ionic and chemical transductions taking place in mucinous ground substance.

FIG. 1 shows the two individual optic tracts that are part of the visual system in the brain. They are a continuation of the optic nerve that relays information from the optic chiasma to the ipsilateral lateral geniculate nucleus (LGN), pretectal nuclei, and superior colliculus. The two individual tracts are the left optic tract and the right optic tract, each of which conveys visual information exclusive to its respective contralateral half of the visual field. Each of these tracts is derived from a combination of temporal and nasal retinal fibers from each eye that corresponds to one half of the visual field. In more specific terms, the optic tract contains fibers from the ipsilateral temporal hemiretina and contralateral nasal hemiretina.

US Patent Application Publication No. 2004/0186533 (the '533 application), whose contents are incorporated by reference, shows a retinal implant to enable vision restoration, which is presented in FIG. 2, wherein a cross-section of the eye is presented showing the lens 208, retina 212, sclera 206, and fovea 213. The retinal implant is subretinal rather than epiretinal, thereby facilitation stimulation of the retinal tissue.

U.S. Pat. No. 5,935,155, whose contents are incorporated herein by reference, describes a retinal implant 220 that is implanted subretinally. A primary coil 232 is located preferably either in an eyeglass lens frame or in a soft contact lens. This coil 232 is used to inductively couple the radio frequency encoded image signal to the secondary coil 230 that, in this embodiment, is implanted behind the iris of the eye. The control electronics 222 is placed in a hermetically sealed package and is coupled to a secondary coil 230 by a coil lead 223 that pierces the sclera 206 at a point near the lens 208. The lead wire 226 passes inside the eye, preferably along the interior wall of the eye, and pierces the retina to pass transretinal to couple the control electronics 222 to the retinal implant 220.

According to the '533 application, as intraocular surgical techniques advanced, it became possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in efforts to restore vision where blindness is caused by photoreceptor degenerative retinal diseases, such as reinitis pigmentosa or to macular degeneration.

The '533 application notes that a variety of retinal diseases cause vision loss or blindness by destruction of the choroid, choriocapillaris, and the outer retinal layers. The outer layers include Bruch's membrane and retinal pigment epithelium, the loss of which results in degeneration of the inner retinal photoreceptor layer. These diseases, however, often spare much of the remaining inner retinal layers of the outer nuclear, outer plexiform, inner nuclear, inner plexiform, ganglion cell, and nerve fiber layers.

The '533 application further notes that efforts to produce vision by retinal electrical stimulation with arrays of stimulating electrodes are primarily placement on the epiretinal or on the subretinal side of the neuroretina. Attempts have been made to produce vision by stimulating various portions of the retina. One attempt involved an externally powered but internally located photosensitive array device with its photoactive surface and electrode surface on opposite sides. The device was to stimulate the nerve fiber layer via direct placement on this layer from the vitreous body side. The device may need to duplicate the neural signals of the nerve fiber layer. The nerve fiber layer generally runs radially with many layers of overlapping fibers from different portions of the retina making selection of the appropriate nerve fiber to stimulate difficult.

I find it desirable to implement a surgical procedure in which the optic nerve and optic tracts serve as a conduit for tunneling or negotiating a nano-fiber optic cable bundle or even electrodes through the optic nerve and optic tract(s) all the way to abut the nuclei of the lateral geniculate body or bodies. Threading the diseased optic nerve with a nano-fiber optic bundle or with electrodes to reach the lateral geniculate body would give the most direct route. The path from the eye to the geniculate body is less than five inches long.

SUMMARY OF THE INVENTION

One aspect of the invention resides in a vision surgical implant tailored to people with damaged optic nerves as suffering from blindness due to glaucoma that includes a vision restoring prosthesis and a transparent casing that encloses the vision restoring prosthesis. The vision restoring prosthesis includes a photoreceptor component and a nano-fiber optic bundle component. The photoreceptor component includes a microelectronic artificial vision array that is powered wirelessly and carries micro photodiodes and has a shape of an intraocular cataract lens. The nano-fiber optic bundle component is configured to negotiate a damaged optic nerve and an optic tract to abut the lateral geniculate nucleus and to stimulate the lateral geniculate nucleus to process vision as the nano-fiber optic bundle abuts the lateral geniculate nucleus.

Another aspect of the invention resides is in a method of placing a vision surgical implant. The method includes the steps of providing a vision restoring prosthesis; enclosing the vision restoring prosthesis with a transparent casing, the vision restoring prosthesis including a photoreceptor component and a nano-fiber optic bundle component, the nano-fiber optic bundle component including nano-fiber optics within a sheath, the nano-fiber optic bundle component extending from the photoreceptor component; wirelessly powering the photoreceptor component, which includes a microelectronic artificial vision array that carries micro photodiodes; implanting the microelectronic artificial vision array behind a pupil of an eye, negotiating a damaged optic nerve and an optic tract with the nano-fiber optic bundle component to abut the nano-fiber optic bundle with a lateral geniculate nucleus; and stimulating the lateral geniculate nucleus with the nano-fiber optic bundle to process vision as the nano-fiber optic bundle component abuts the lateral geniculate nucleus.

BRIEF DESCRIPTION OF THE DRAWING

For a better understanding of the present invention, reference is made to the following description and accompanying drawing, while the scope of the invention is set forth in the appended claims.

DETAILED DESCRIPTION OF THE INVENTION

Figure 1:
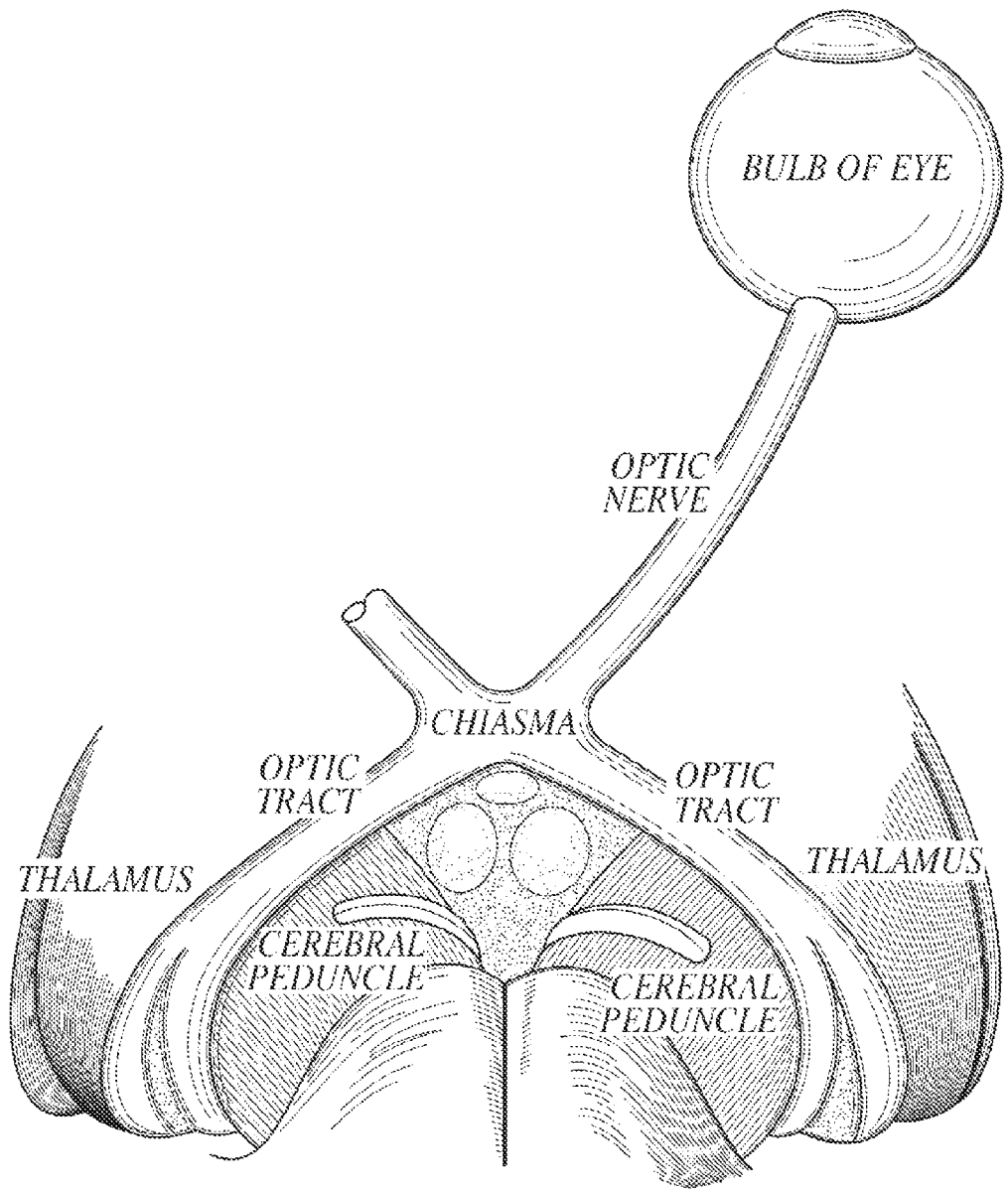
FIG. 1 is a schematic view of the left optic nerve and optic tracts of the visual system in the brain.
Figure 2:
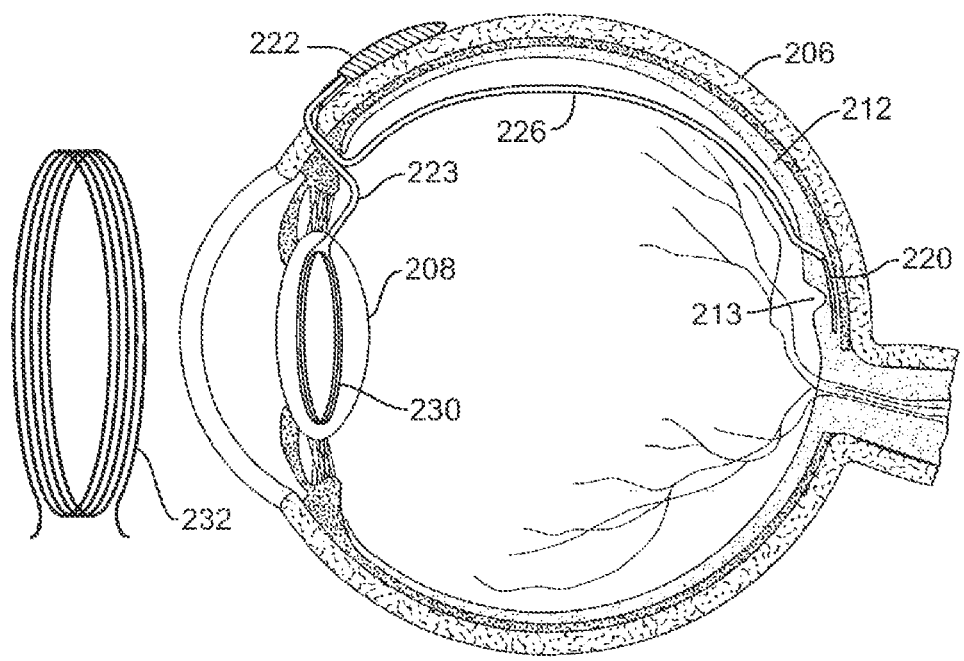
FIG. 2 is a cross-sectional view of an eye showing placement of a suretinal implant according to US Patent Application Publication No. US2004/0186533.
Figure 3:
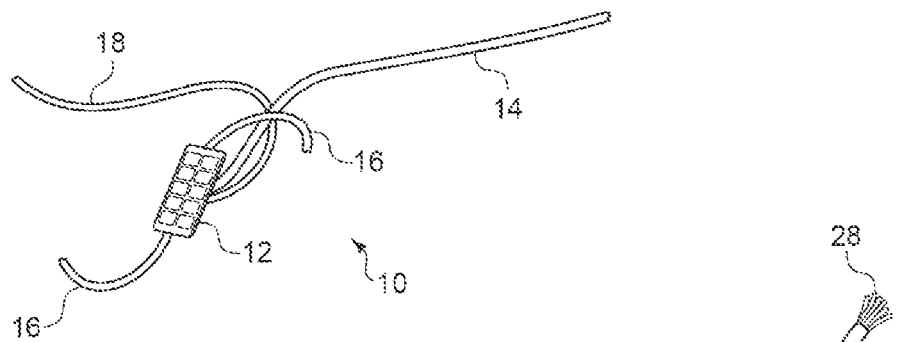
FIG. 3 is a front view of an artificial vision restoring prosthesis in accordance with the invention.

Turning to FIG. 3, a vision restoring prosthesis 10 is shown that is bio-compatible, durable and inert for restoring vision from blindness caused by atrophy of the optic nerve—glaucoma being the most common cause of optic nerve death.

The vision restoring prosthesis 10 is a surgically implanted device to serve persons who are blind from glaucoma—a condition of damaged optic nerves—and for others with like conditions whose optic nerves are not functioning because of disease or trauma, including people whose eyes were nonsighted and shriveled (a phthisus bulbi condition) or even absent. With failed optic nerve, an alternate way is to bypass it and connect the images to the vision centers of the lateral geniculate body nuclei.

The vision restoring prosthesis 10 includes a photoreceptor component 12 and a nano-fiber optic cable bundle component 14. The photoreceptor component 12 is elongated between opposite ends and includes a microelectronic artificial vision array that is powered wirelessly and carries micro photodiodes and has a shape of an intraocular cataract lens. The nano-fiber optic cable bundle component 14 is configured to stimulate a lateral geniculate nucleus to process vision as the nano-fiber optic bundle abuts the lateral geniculate nucleus. Two haptic loops 16 extend outwardly each from opposite ends of the photoreceptor component 12. A power cable 18 from a power supply (not shown) may be provided to power the vision restoring prosthesis.

Figure 4:
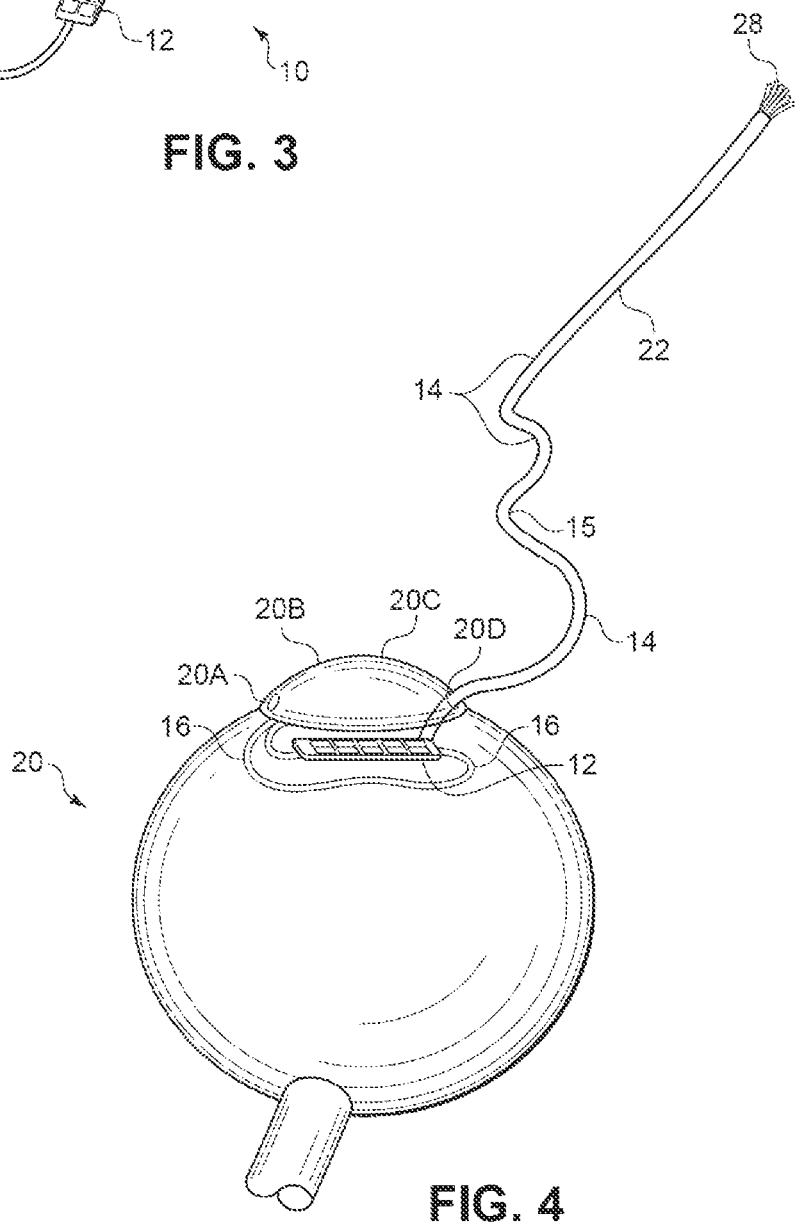
FIG. 4 is a cross-sectional view of an eye showing placement of the artificial vision restoring prosthesis of FIG. 3.

Turning to FIG. 4, the eye 20 has an iris 20A, a cornea 20B and a pupil 20C. The microelectronic artificial vision array of the photoreceptor component 12 is implanted behind the pupil 20C of the eye 20 in the same manner that an intraocular lens is implanted behind the pupil for cataract surgery to offer lensectomy in the posterior capsule with the nano-fiber optic cable bundle component 14 coming out of it through the scheral tunnel. This nano-fiber optic cable bundle component 14 substitutes for the optic nerve and would be surgically guided and implanted directly in the lateral geniculate body, which is a vision area of the thalamus of the brain.

Preferably, the nano-fiber optic cable bundle component 14 is made of a bundle of silicon oxide ($SiO_2$) microfibers connecting the array of micro photodiodes of the photoreceptor component with the nuclei of lateral geniculate body, possibly using an optical network on a chip, which is a type of multi-processor system on a micro-chip. The vision restoring prosthesis 10 is preferably encased or enclosed in a transparent poly methyl methacrylate casing 22. The nano-fiber optic cable bundle component 14 has an orbital portion 15 that is softer than the more distal portion that is flexible.

To reach the brain tissue of the lateral geniculate body, optic nerve fenestration surgery is performed by implementing a surgical procedure in which the optic nerve serves as a conduit for tunneling or navigating the nano-fiber optic cable bundle or even electrodes through the optic nerve all the way to abut the nuclei of the lateral geniculate body nucleus 28. The optic nerve fenestration surgical procedure avoids craniotomy and avoids the need to cut into bulky brain tissue.

Optic nerve fenestration is an opening that is created surgically through the optic nerve. This can be carried out with the aid of Stryker iNtellect cranial navigation software, magnetic resonance imaging (MR) and/or computerized tomography (CT) scan for guidance by adopting techniques akin to coronary artery stent insertion on a miniaturized scale. The Styker iNtellect cranial navigation software integrates image-guided surgery into current conventional neurosurgical practices.

The nano-fiber optic cable bundle component 14 is pushed to enter the optic nerve in the middle of the optic nerve and not along its side under the dura mater so as to avoid causing cerebrospinal fluid leak. An iridotomy procedure may be performed to make puncture-like openings 20D through the iris 20A without the removal of its tissue to accommodate passage of the nano-fiber optic cable bundle 14 through the iris 20A to reach the lateral geniculate body nucleus 28.

Figure 5:
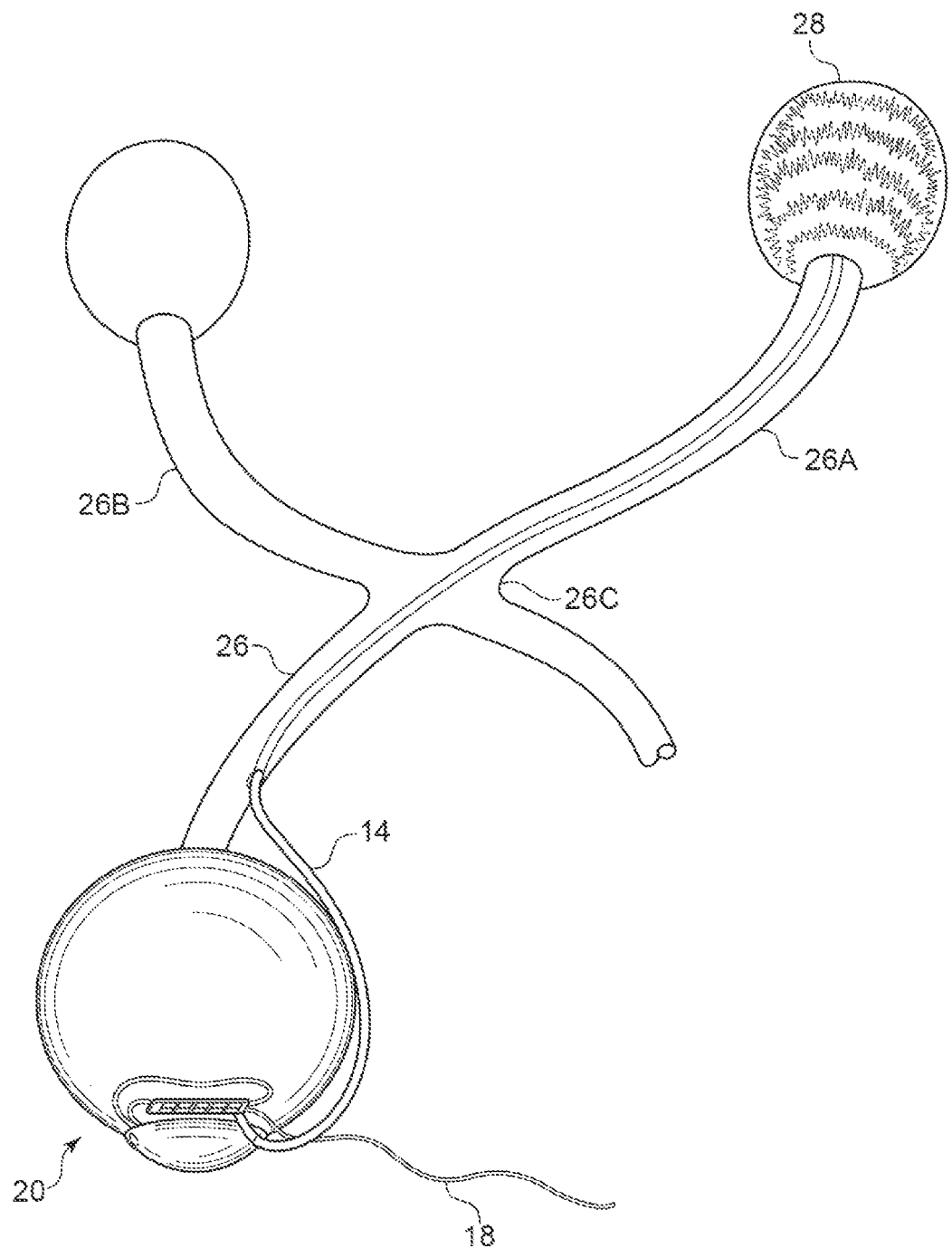
FIG. 5 is a cross-sectional view of an eye with the artificial vision restoring prosthesis in place as in FIG. 4, but for a single nano-fiber optic cable embodiment.

In the case of FIG. 5, a single cable is utilized as the nano-fiber optic cable bundle component 14 to pass through the optic nerve 26 and an optic tract 26A to reach the nuclei of the lateral geniculate body nucleus 28. A power supply cable 18 goes to a coil implanted at the temple under the temporalis muscle fascia. The optic chiasm or optic chiasma 26C is that part of the brain where optic nerves partially cross to enter separate optic tracts 26A, 26B. The optic chiasm is located immediately below the hypothalamus.

Figure 6:
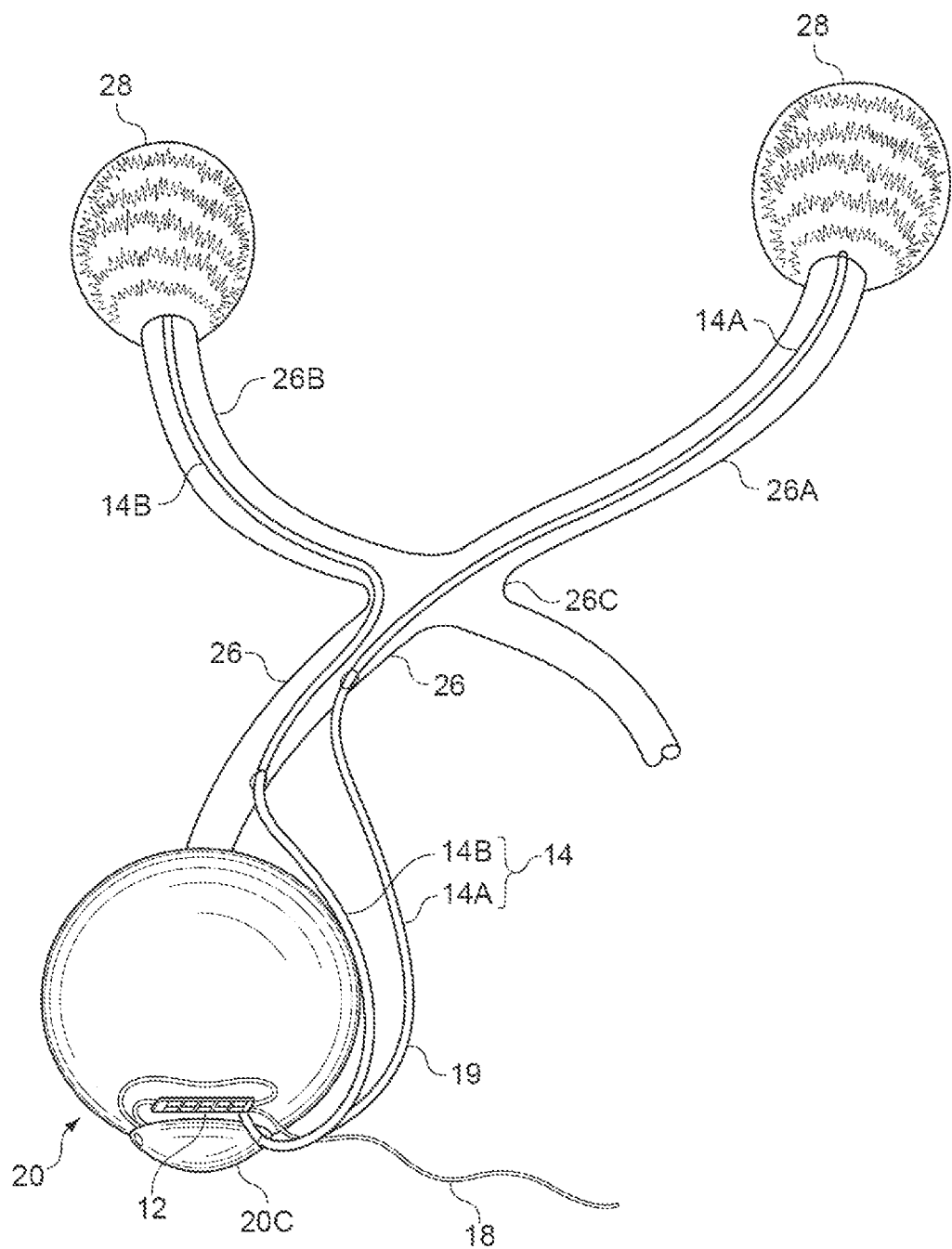
FIG. 6 is a cross-sectional view of an eye with the artificial vision restoring prosthesis in place as in FIG. 4, but for a twin nano-fiber optic cable embodiment.

In the case of FIG. 6, twin cables are utilized as the nano-fiber optic cable bundle 14 with one 14A going straight and the other 14C crossed to reach opposite lateral geniculate bodies via passing through the optic nerve 26 and two optic tracts 26A, 26B.

Figure 7:
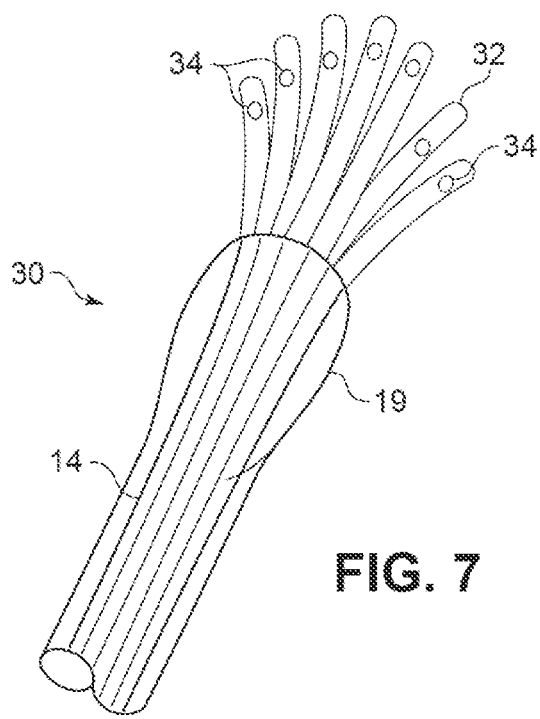
FIG. 7 is a front view of a head of a bundle of silica fiber optic nano-fibers with side holes.
Figure 8:
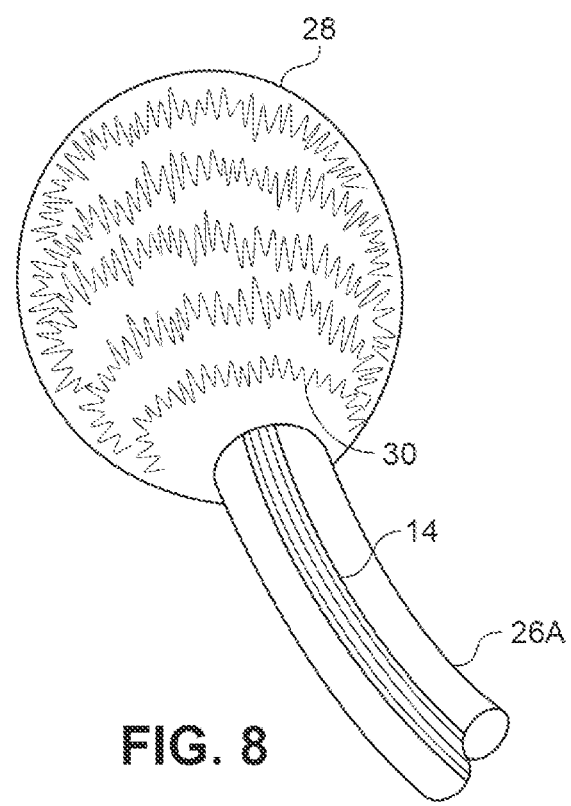
FIG. 8 is a schematic view of an optic tract and lateral geniculate body with the nano-fiber optic cable extending through the optic tract to abut layers of neuronal nuclei of the lateral geniculate nucleus.

FIG. 7 shows the distal end of a bundle of the nano-fiber optic bundle 14 designed to rest in the lateral geniculate body nucleus 28. The distal end of the nano-fiber optic bundle 14 has silica fibers 30 whose distal end tips 32 project out of the polymethyl methacrylate casing 19 or sheath by a distance and is equipped with side holes 34 spaced apart from each other on the side of the silica fibers along the distance to allow light to exit horizontally from the side holes 34 into the cupola of the lateral geniculate body nucleus 28.

Preferably, the visual images from the eye reach the lateral geniculate body nuclei as processed light via the nano-fiber optic cable bundle 14 rather than as electric stimulus with electrodes as the latter might cause overheating of tissues in the brain.

It is important to the entire glaucoma vision implant device to be entirely buried in the tissues and not to have any exposed parts to the outside so as to avoid the risk of infection and of carrying infection into the brain. This is akin to how the lumbar peritoneal shunt is conceptualized.

A shunt is a medical device that creates an unnatural opening between two interior parts of the body. It is used to help drain certain areas of the body when there is fluid build up, and to help correct problems associated with that fluid build up. A lumbar peritoneal shunt is a shunt that is inserted into the subarachnoid space between two vertebrae. This is the area around the spinal cord where cerebrospinal fluid, the fluid that bathes the brains and the spinal cord, can build up. The lumbar peritoneal shunt is a long tube that wraps around the body and eventually emerges into the peritoneum, which is the cavity in the torso where all of the abdominal organs reside.

In cases of a phthisis bulbi deformed or absent eye, the unit of the microelectronic artificial vision array with micro photodiodes, which is encased in transparent polymethyl methacrylate and has a shape like an outdoor reflector light, is placed subconjunctivally next to the eye affixed in the tendon of lateral rectus muscle. Intraocular lens implants area made of polymethyl methacrylate. If desired, other kinds of transparent sheathing materials could be used instead of polymethyl methacrylate, provided such transparent sheathing materials have comparable qualities to polymethyl methacrylate of being inert, bio-compatible and durable.

The unit would have to stay under the conjunctive. The conjunctive is translucent so a person would see through the conjunctive in a manner analogous to seeing through a shower curtain or better if the conjunctive is treated with clarifying drops. In the case of the absent eye, the unit is placed under the conjunctive as the front part of the orbital implant in the eye socket.

An alternative artificial vision device would be a system of mounting micro-video cameras on eye contact lens or, on eyeglasses equipped with knobs to control operation and powered by batteries of a battery pack that are in or on the eyeglass frame such as its temple bar. The cameras send the images to an intraocular lens implant, which would have pixel-like photodiodes with technology of complementary oxide semiconductor (CMOS) analogy system. From there, the image would be passed via nano-fiber optic bundle filaments in cable the same way as in any of the embodiments of FIGS. 3-10, i.e., surgically pushed inside the body of the optic tract of the optic nerve to abut the lateral geniculate body nuclei to elicit vision sensation.

The vision restoration method includes implanting a vision restoring prosthesis 10 of FIG. 3 behind a pupil of an eye. The vision restoring prosthesis 10 is enclosed by a transparent casing 19 of FIG. 4 to be sturdy yet flexible and has a photoreceptor component and a nano-fiber optic cable bundle component 14. Further, the photoreceptor component 12 is wirelessly powered and includes a microelectronic artificial vision array that carries micro photodiodes and has a shape of an intraocular cataract lens.

The a nano-fiber optic cable bundle component 14 extends through the optic tract 26 to have silica fibers 30 whose distal end tips 32 abut against neuronal layers of nuclei of the lateral geniculate nucleus 38 of the thalamus of the eye in the manner of FIG. 4. The lateral geniculate body nucleus 28 is stimulated by the implant prosthesis to process vision as the nano-fiber optic cable bundle component 14 abuts the lateral geniculate body nucleus 28.

Figure 9:
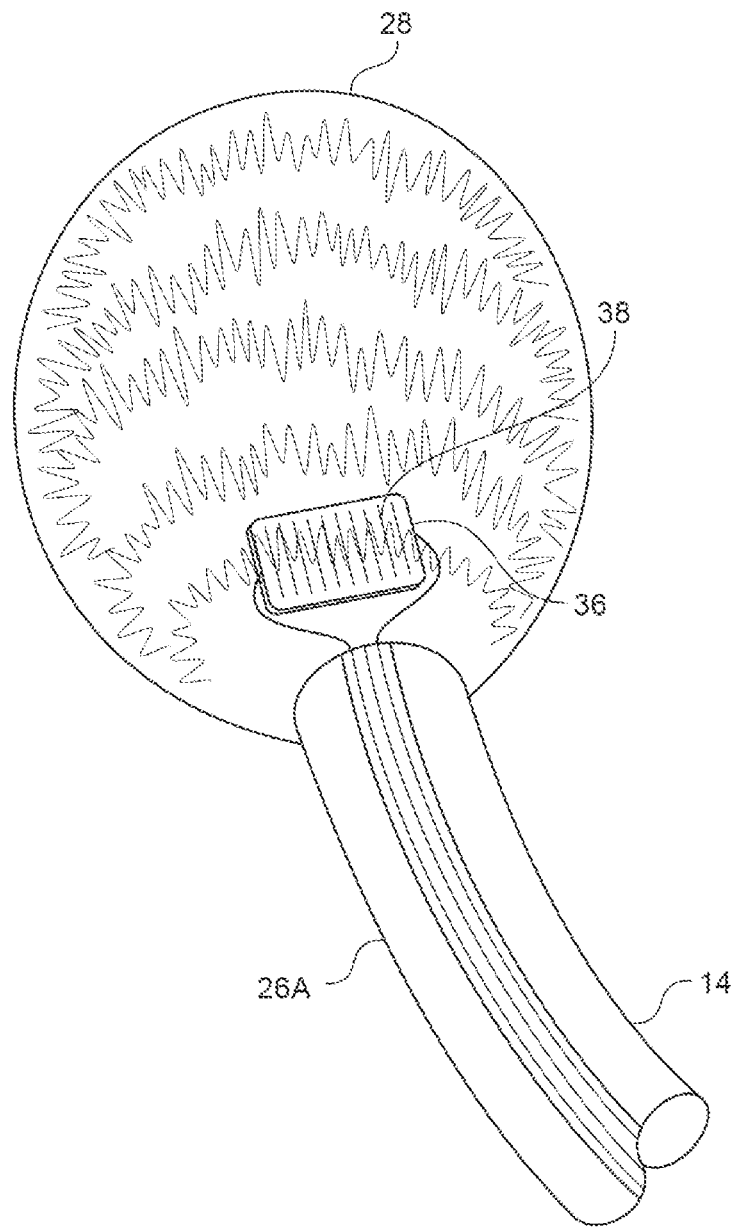
FIG. 9 is a schematic view of an optic tract and lateral geniculate body with the nano-fiber optic cable extending through the optic tract to alternately abut with a photodiode chip layers layers of neuronal nuclei of the lateral geniculate nucleus.

As an alternative, the nano-fiber optic cable bundle component 14 may be equipped at its distal end with a photodiode chip 36 of FIG. 9 to which is connected ends of the fiber optic nano-fibers and arranged so that the photodiode chip 36 abuts the lateral geniculate body nucleus 28. The photodiodes 38 of the photodiode chip 36 extend forwardly of a remainder of the photodiode chip 36 and are exposed to emit light preferably horizontally into the lateral geniculate body nucleus 28.

The artificial vision photodiode array of the photoreceptor component 12 is implanted behind the pupil in sulcus if it is a pliable model or in a capsular bag following lensectomy by phacoemulsification technique or by extracapular technique via scleral tunnel incision. The nano-fiber optic cable of the nano-fiber optic bundle component 14 and the power supply cable 18 are dimensioned to be passed through peripheral iridotomy into that tunnel and out of the eye. The implant is surrounded in the posterior chamber by liquid tissues, which would keep it from overheating. Scleral tunnel would be sutured tightly around the fiber optic cable 14 to prevent aqueous leaks.

To reach the optic nerve behind the eye, a method of detaching the medial rectus muscles or a lateral orbitotomy is performed. On the other hand, a lateral orbitotomy is a wellrecognized method of improving orbital access, such for the removal of orbital tumors and foreign bodies.

A slit is made in the optic nerve, and with the aid of the Stryker iNtellect Cranial navigation system, a flexible trochar then guides by stent, threading the nano-fiber optic cable to abut deep into the lateral geniculate body nucleus.

The nano-fiber optic cable would have two arms. One arm would be guided nasally to enter the chiasma to reach the opposite lateral geniculate body nucleus. The other arm would be guide on the lateral side of the optic nerve to go to the ipsilateral geniculate body nucleus. This is to allow for the visual field not to be one sided (i.e., hemianopic).

Figure 10:
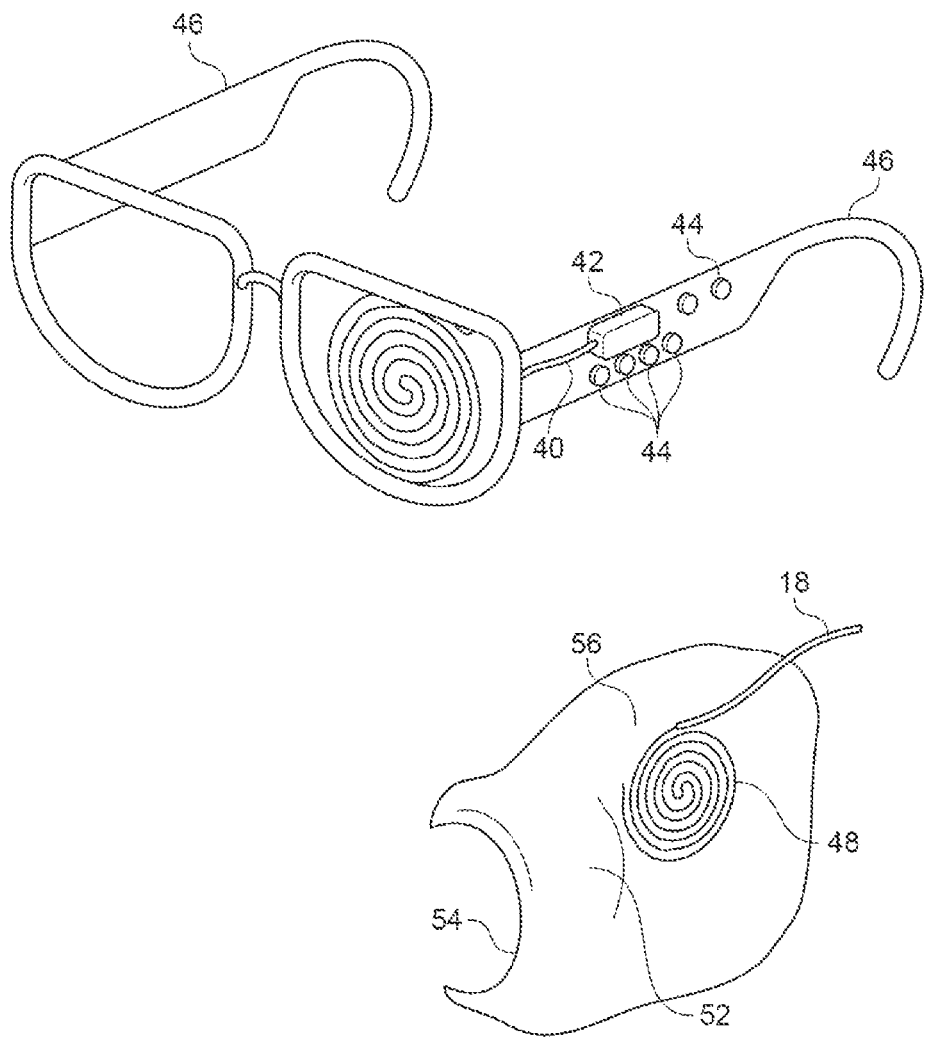
FIG. 10 is an isometric vie of eyeglasses equipped with means for powering wirelessly (e.g., a transdermal induction transmitter with a battery pack and operation control knobs and a power receiving coil with power supply cable implanted under the temporalis fascia in the area of the temple.

Turning to FIG. 10, the glaucoma vision implant could be powered wirelessly by a transdermal induction transmitter 40 with battery pack 42 and operating control knobs 44 in any eyeglass frame 46 and a power supply component that includes a power receiving coil 48 with power supply cable 18 implanted under the temporalis fascia 52 in the area of the temple by the orbital rim 54.

The fascia of the temporalis muscle 52 is a broad, strong tenineous aponeurosis. There is a natural space under the temporalis fascia 52 between it and the periosteum 56. An incision through the skin of the temple two inches backward from the lateral orbital rim 54 down to the periosteum 56 will allow the coil power receiving implant to be slipped in the secure position between the temporalis fascia above the power receiving coil 48 and the periosteum 56 behind or under it.

The power receiving coil 48 so implanted would have the added benefit of being, vis-à-vis side of the eye glasses frame containing the transdermal inductive transmitter system, a far shorter route of transmitting the electric power.

It is known from U.S. Pat. No. 6,673,064 to make a distal tip more flexible and less stiff than the rest of an elongated shaft to aid in being pushable to enable pushing the tip into a desired site in the body even though the tip negotiates bends to reach the desired site. Such may be adopted for the present invention by enhancing sturdiness of the cable by providing the cable with a sheath along a majority of its length and encasing the sheath with the polymethyl methacrylate and allowing the distal tip as per FIGS. 7-8 to have ends of the nano-optical fibers protrude out of the sheath, yet be encased by the polymethyl methacrylate casing. In the case of FIG. 9, the casing renders the cable sufficiently sturdy to enable the photodiode to be pushed to negotiate the optic nerve and optic tract.

While the foregoing description and drawings represent the preferred embodiments of the present invention, various changes and modifications made be made without departing from the scope of the present invention.

What is claimed is:

1. A glaucoma vision implant, comprising
   a vision restoring prosthesis, and
   a transparent casing that encloses the vision restoring prosthesis, the vision restoring prosthesis including a photoreceptor component and a nano-fiber optic bundle component, the photoreceptor component including a microelectronic artificial vision array that is powered wirelessly and carries micro photodiodes, said nano-fiber optic cable bundle component including a nano-fiber optical cable within a sheath and being configured to extend from the photoreceptor component, said nano-fiber optic cable bundle component being configured to negotiate a damaged optic nerve and an optic tract of an eye until abutting with a lateral geniculate nucleus of the optic nerve of the eye, said nano-fiber optic bundle component being further configured with the photoreceptor component powered to emit light, which stimulates the lateral geniculate nucleus to process vision.

2. The glaucoma vision implant of claim 1, wherein the transparent casing includes material that is methyl methacrylate.

3. The glaucoma vision implant of claim 1, wherein the photoreceptor component is elongated with a shape of an intraocular cataract lens; and loop haptics that extend outward from opposite ends of the photo receptor component.

4. The glaucoma vision implant of claim 1, wherein the nano-fiber optic cable bundle component also includes electrodes that abut the lateral geniculate nucleus and are configured to stimulate the lateral geniculate nucleus to process vision.

5. The glaucoma vision implant of claim 1, wherein the nano-fiber optic cable bundle component includes two cables each dimensioned and configured to negotiate through an optic nerve and through respective ones of two optic tracts from the photoreceptor component to reach respective ones of opposite lateral geniculate nucleus bodies, the optic fibers being further configured to emit light that stimulates the opposite lateral geniculate nucleus bodies to process vision as the two cables abut the opposite lateral geniculate nucleus bodies.

6. The glaucoma vision implant of claim 1, wherein the nano-optic cable bundle component has distal ends of the nano-fiber optics protruding outward from an end of the sheath by a distance so as to have an exposed side portion that extends the distance, the side portion having a plurality of side holes that allow the light to exit.

7. The glaucoma vision implant of claim 1, further comprising
   a power supply component arranged to supply power to the photoreceptor component and the nano-fiber optic cable bundle component, both the power supply component and the nano-fiber optic cable bundle component having respective cables that extend through peripheral iridotomy.

8. The glaucoma vision implant of claim 1, further comprising
   a power supply component arranged to supply power to the photoreceptor component and the nano-fiber optic bundle component, said power supply component including a power receiving coil; and
   means for wirelessly powering the power receiving coil through induction.

9. A method of placing a vision surgical implant, comprising the steps of:
   providing a vision restoring prosthesis;
   enclosing the vision restoring prosthesis with, a transparent casing, the vision restoring prosthesis including a photoreceptor component and a nano-fiber optic cable bundle component, the nano-fiber optic cable bundle component including nano-fiber optics within a sheath, the nano-fiber optic cable bundle component extending from the photoreceptor component;
   wirelessly powering the photoreceptor component, which includes a microelectronic artificial vision array that carries micro photodiodes;
   implanting the microelectronic artificial vision array behind a pupil of an eye;
   negotiating a damage optic nerve and an optic tract with the nano-fiber optic cable bundle component until the nano-fiber optic cable bundle component abuts with a lateral geniculate nucleus of an optic nerve of the eye; and emitting light, which stimulates the lateral geniculate nucleus to process vision, from the nano-fiber optic cable bundle component with the photoreceptor component powered as the nano-fiber optic cable bundle component abuts the lateral geniculate nucleus.

10. The method of claim 9, wherein the transparent casing includes material that is methyl methacrylate.

11. The method of claim 9, wherein the photoreceptor component is elongated with a shape of an intraocular cataract lens; and
    loop haptics extending outward from opposite ends of the photo receptor component.

12. The method of claim 9, wherein the nano-fiber optic cable bundle component includes electrodes, further comprising
    abutting the electrodes of the nano-fiber optic cable bundle component with the lateral geniculate nucleus and
    stimulating the lateral geniculate nucleus to process vision.

13. The method of claim 9, further comprising
    negotiating each of two cables of the nano-fiber optic cable bundle component through the optic nerve and through respective ones of the two optic tracts from the photoreceptor component to reach respective ones of two opposite lateral geniculate nucleus bodies; and
    emitting the light from the two cables as the two cables abut the opposite lateral geniculate nucleus bodies.

14. The method of claim 9, wherein the nano-optic cable bundle component has distal ends of the nano-fiber optics protruding outward from an end of the sheath by a distance so as to have an exposed side portion that extends the distance, the side portion having a plurality of side holes that allow the light to exit.

15. The method of claim 9, further comprising
    arranging a power supply component to supply power to the photoreceptor component and the nano-fiber optic cable bundle component, both the power supply component and the nano-fiber optic cable bundle component having respective cables that extend through peripheral iridotomy.

16. The method of claim 9, further comprising
    arranging a power supply component to supply power to the photoreceptor component and the nano-fiber optic bundle component, said power supply component including a power receiving coil; and
    wirelessly powering the power receiving coil through induction.

* * * * *